United States Patent [19]

Kita et al.

[11] Patent Number: 4,514,501
[45] Date of Patent: Apr. 30, 1985

[54] METHOD FOR CULTIVATION OF MICROORGANISM

[75] Inventors: Yukio Kita, Tokyo; Kazuo Koide, Urayasu; Kouki Horiko, Tokyo, all of Japan

[73] Assignee: Oji Paper Company, Ltd., Tokyo, Japan

[21] Appl. No.: 348,194

[22] Filed: Feb. 12, 1982

[30] Foreign Application Priority Data

Feb. 21, 1981 [JP] Japan .................. 56-23672

[51] Int. Cl.$^3$ .................. C12N 1/24; C12N 1/20; C02F 3/34; D21C 11/00
[52] U.S. Cl. .................. 435/251; 435/804; 435/253; 435/830; 435/832; 435/840; 435/843; 210/611; 210/928; 162/16
[58] Field of Search .............. 435/251, 252, 253, 804, 435/830, 832, 840, 843; 210/611, 928; 162/16

[56] References Cited

U.S. PATENT DOCUMENTS

| | | | |
|---|---|---|---|
| 2,382,010 | 8/1945 | Hodges | 210/928 |
| 2,431,163 | 11/1947 | Boehm et al. | 435/252 |
| 3,737,374 | 6/1973 | Stern et al. | 210/611 |
| 3,778,349 | 12/1973 | Carta | 435/804 |
| 3,949,086 | 4/1976 | Wolfson | 162/161 |
| 4,030,968 | 6/1977 | Goel et al. | 162/16 |
| 4,370,199 | 1/1983 | Orndorff | 162/161 |

FOREIGN PATENT DOCUMENTS

| | | | |
|---|---|---|---|
| 68393 | 6/1981 | Japan | 435/832 |
| 0590387 | 1/1978 | U.S.S.R. | 435/251 |

OTHER PUBLICATIONS

Buckman et al., "Deposits Control" in Papermaking and Paperboard Making, vol. III, by MacDonald et al., ed., (1970), pp. 103–107.

Kanamitsu, "Microbial Raw Sewage Treatment", Japan Kokai 75/125,551, (1975), Chemical Abstracts, 84: 65087n.

Rast et al., "Bacterial Degradation of Model Compounds for Lignin and Chlorophenol Derived Lignin Bound Residues", FEMS Microbiol. Letters, 8(4), (1980), pp. 259–263.

*Primary Examiner*—Lionel M. Shapiro
*Assistant Examiner*—J. E. Tarcza
*Attorney, Agent, or Firm*—Armstrong, Nikaido, Marmelstein & Kubovcik

[57] ABSTRACT

A method for cultivating, under alkaline conditions, microorganisms in a culture medium containing, as a carbon source, the extracted liquor or spent liquor derived from alkaline pulping is presented. In this cultivation, organic acids contained in the extracted liquor or spent liquor can be effectively utilized. Typical microorganisms cultured are bacteria belonging to the genera Bacillus, Arthrobacter, Corynebacterium and Brevibacterium.

2 Claims, No Drawings

METHOD FOR CULTIVATION OF MICROORGANISM

The present invention relates to a method for cultivating microorganisms.

As is known, fibrous materials such as wood and non-wood plants, etc. are cooked under a high alkaline condition at an elevated temperature and pressure by the kraft pulping process, soda pulping process, oxygen-alkali pulping process, alkaline sulfite pulping process, or other alkaline pulping process, a large amount of the hemicellulose component and a portion of the cellulose component in addition to the lignin component contained in the fibrous materials are solubilized and decomposed, thereby dissolving in the extracted liquor or the spent liquor.

As is disclosed in "Tappi" Vol. 59, No. 9, 118–121 (1976), various organic acids including isosaccharinic acids and metasaccharinic acids mainly derived from carbohydrates are formed and dissolved in spent liquor in the course of alkaline pulping. The mechanism of decomposition and dissolution of carbohydrates in natural fibrous materials is known as the so-called peeling reaction. However, it has not been reported in the prior arts that these organic acids can be utilized under alkaline conditions by microorganisms.

The initial pH of an alkaline cooking liquor is approximately 14 due to the presence of caustic alkali. Although the caustic alkali contained in the cooking liquor is partially consumed by organic acids formed in the course of cooking, the liquor extracted from the cooking system at the initial and intermediate cooking stages and the spent liquor generally contain remaining alkali in a concentration of 2 through 30 g/l in terms of $Na_2O$ and still are strongly alkaline having a pH of 10 through 14. Thus, the extracted liquor or the spent liquor derived from the alkaline pulping contain, as an organic substance, lignin and various organic acids and also contain a large amount of various salts.

The cellulose rich insoluble component obtained from the alkaline cooking is directly utilized as pulp in the production of paper. However, the remaining extracted liquor and spent liquor have heretofore been burned after concentration. Thus, only combustion energy has been recovered from the organic substances and only cooking chemicals have been recovered from the inorganic substances.

Accordingly, the object of the present invention is to effectively utilize the above-mentioned extracted liquor and spent liquor so as to cultivate microorganisms by utilizing the organic substances, especially various organic acids contained in the extracted liquor or spent liquor in an alkaline region i.e., without neutralizing the alkaline extracted liquor or spent liquor.

Other objects and advantages of the present invention will become clear from the following description.

In accordance with the present invention, there is provided a method for cultivating microorganisms comprising the steps of:

inoculating the microorganisms into a culture medium containing, as a carbon source, the extracted liquor or the spent liquor derived from alkaline pulping; and cultivating the inoculated microorganisms in the culture medium, whereby organic acids contained in the extracted liquor or spent liquor are utilized.

The inventors have studied the microorganisms which may be commercially produced under alkaline conditions, desirably a pH of 8.0 through 12.5, using the alkaline extracted liquor or spent liquor containing salts in an high concentration. As a result of the classification and search of numerous strains of bacteria isolated from natural soils, the bacteria belonging to genera Bacillus, Arthrobacter, Corynebacterium or Brevibacterium, which are viable in an alkaline extracted liquor or spent liquor have been isolated from the natural soils at Shinonome, Koto-ku, Tokyo, Japan.

Typical examples of the bacteria usable in the present invention are the bacteria belonging to: Bacillus such as *Bacillus* sp. FERM-P No. 5861, which has been deposited since Jan. 30, 1981 in the Fermentation Research Institute (FRI) in Japan (all the numbers quoted as "FERM-P" hereinafter refer to the deposition numbers of said Institute) and *Bacillus* sp. FERM-P No. 5862 deposited on the same date: Arthrobacter such as *Arthrobacter* sp. FERM-P No. 5683 deposited on the same date, and *Arthrobacter* sp. FERM-BP No. 88, which has been deposited since Feb. 2, 1982 in the Fermentation Research Institute (FRI) (i.e. International Depository Authority under Budapest Treaty) as Tsukuba in Japan; *Corynebacterium* sp. FERM-BP NOs. 89 and 90 deposited on Feb. 2, 1982 in FRI under Budapest Treaty; and Brevibacterium FERM-BP Nos. 91 and 92 deposited on Feb. 2, 1982 in FRI under Budapest Treaty. All the depositions were made by Mr. Yukio Kita, one of the inventors.

The morphological characteristics of these bacteria are shown below. The test methods of these morphological characteristics and the classification of the bacteria were carried out according to the descriptions in N. R. Smith, R. E. Gordon & F. E. Clark "Aerobic Sporeforming Bacteria (United States Department of Agriculture, November, 1952)" and "Bergey's Manual of Determinative Bacteriology (8th edition, 1974)".

MORPHOLOGICAL, CULTURAL AND BIOCHEMICAL CHARACTERISTICS OF BACILLUS FERM-P NO. 5861

(a) Morphological characteristics

| | | |
|---|---|---|
| 1 | Cell form and size | rods, 0.7–0.9 × 1.8–3.0μ |
| 2 | Cell pleomorphism | non pleomorphic |
| 3 | Motility | motile, peritrichous |
| 4 | Sporulation | endospore-forming, sporangia not definitely swollen, spores 0.6–0.9 × 1.0–1.5μ, oval, central |
| 5 | Gram stain | positive |
| 6 | Acid fast stain | non acid fast |

(b) Cultural Characterization

| | | Cultural characterization pH of culture media | |
|---|---|---|---|
| | Media | pH 7.0 | pH 10.0* |
| 1 | Nutrient agar plate | poor growth | good growth, circular, flat to raised, filamentous, cream colored, opaque, smooth, glistening |
| 2 | Nutrient agar slant | poor growth | good growth, spreading |
| 3 | Nutrient broth | poor growth | moderately tubid, no surface growth, sediment |
| 4 | Gelatin stab | poor growth | surface growth, liquefaction, crateriform |
| 5 | Litmus milk | no change | no change |

(c) Biochemical characteristics*

| | | |
|---|---|---|
| 1 | Reduction of nitrate to nitrite | + |
| 2 | Nitrate respiration | − |
| 3 | Methyl red test | cannot observe the |

MORPHOLOGICAL, CULTURAL AND BIOCHEMICAL CHARACTERISTICS OF BACILLUS FERM-P NO. 5861 -continued

| | | |
|---|---|---|
| | | change of color because of alkaline medium |
| 4 | Voges-Proskauer test | − |
| 5 | Production of indole | − |
| 6 | Production of H₂S | − |
| 7 | Hydrolysis of starch | + |
| 8 | Utilization of citrate | |
| | Koser's citrate agar | + |
| | Christensen's citrate agar | + |
| 9 | Utilization of inorganic nitrogen source | utilize nitrates and ammonium salts |
| 10 | Production of pigment | none |
| 11 | Urease test | − |
| 12 | Oxidase test | + |
| 13 | Catalase test | + |
| 14 | pH and temperature for growth | |
| | pH for growth | 7.5-11.5 Optimum pH about 10 |
| | Temperature for growth | up to 50° C. Optimum temperature about 40° C. |
| 15 | Oxygen relation | aerobic |
| 16 | O-F test (Hugh and Leifson's medium) | oxidative |
| 17 | Utilization of carbohydrates | |
| | (1) L-Arabinose | + |
| | (2) D-Xylose | + |
| | (3) D-Glucose | + |
| | (4) D-Mannose | + |
| | (5) D-Fructose | + |
| | (6) D-Glactose | + |
| | (7) Maltose | + |
| | (8) Sucrose | + |
| | (9) Lactose | − |
| | (10) Trehalose | − |
| | (11) D-Sorbitol | + |
| | (12) D-Mannitol | + |
| | (13) Inositol | + |
| | (14) Glycerol | + |
| | (15) Starch | + |
| 18 | Another characteristics | good growth in 7% NaCl nutrient broth |

*Na₂CO₃ (1%) was added to the media.
Symbols: +, positive; −, negative

MORPHOLOGICAL, CULTURAL AND BIOCHEMICAL CHARACTERISTICS OF BACILLUS FERM-P NO. 5862

(a) Morphological characteristics

| | | |
|---|---|---|
| 1 | Cell form and size | rods, 0.7-0.8 × 2.0-3.5μ |
| 2 | Cell pleomorphism | non pleomorphic |
| 3 | Motility | motile, peritrichous |
| 4 | Sporulation | endospore forming, sporangia not definitely swollen, spores 0.6-0.9 × 1.0-1.5μ, oval, central |
| 5 | Gram stain | positive |
| 6 | Acid fast stain | non acid fast |

(b) Cultural Characterization

| | | Cultural characterization pH of culture media | |
|---|---|---|---|
| | Media | pH 7.0 | pH 10.0* |
| 1 | Nutrient agar plate | very poor growth | good growth, circular, flat to raised, filamentous, cream colored, opaque, smooth, glistening |
| 2 | Nutrient agar slant | very poor growth | good growth, spreading |
| 3 | Nutrient broth | very poor growth | moderately tubid, no surface growth, sediment |
| 4 | Gelatin | very poor | surface growth, liquefaction, |

MORPHOLOGICAL, CULTURAL AND BIOCHEMICAL CHARACTERISTICS OF BACILLUS FERM-P NO. 5862 -continued

| | | | |
|---|---|---|---|
| 5 | Litmus milk | stab growth no change | crateriform no change |

(c) Biochemical characteristics*

| | | |
|---|---|---|
| 1 | Reduction of nitrate to nitrite | + |
| 2 | Nitrate respiration | − |
| 3 | Methyl red test | cannot observe the change of color because of alkaline medium |
| 4 | Voges-Proskauer test | − |
| 5 | Production of indole | − |
| 6 | Production of H₂S | + |
| 7 | Hydrolysis of starch | + |
| 8 | Utilization of citrate | |
| | Koser's citrate agar | + |
| | Christensen's citrate agar | + |
| 9 | Utilization of inorganic nitrogen source | utilize nitrates and ammonium salts |
| 10 | Production of pigment | none |
| 11 | Urease test | − |
| 12 | Oxidase test | + |
| 13 | Catalase test | + |
| 14 | pH and temperature for growth | |
| | pH for growth | 7.5-12.0 Optimum pH about 10 |
| | Temperature for growth | up to 50° C. Optimum temperature about 40° C. |
| 15 | Oxygen relation | aerobic |
| 16 | O-F test (Hugh and Leifson's medium) | oxidative |
| 17 | Utilization of carbohydrates | |
| | (1) L-Arabinose | + |
| | (2) D-Xylose | + |
| | (3) D-Glucose | + |
| | (4) D-Mannose | + |
| | (5) D-Fructose | + |
| | (6) D-Glactose | + |
| | (7) Maltose | + |
| | (8) Sucrose | + |
| | (9) Lactose | − |
| | (10) Trehalose | + |
| | (11) D-Sorbitol | + |
| | (12) D-Mannitol | − |
| | (13) Inositol | + |
| | (14) Glycerol | − |
| | (15) Starch | + |
| 18 | Another characteristics | good growth in 7% NaCl nutrient broth |

*Na₂CO₃ (1%) was added to the media.
Symbols: +, positive; −, negative

MORPHOLOGICAL, CULTURAL AND BIOCHEMICAL CHARACTERISTICS OF ARTHROBACTER FERM-P NO. 5863

(a) Morphological characteristics

| | | |
|---|---|---|
| 1 | Cell form and size | rods, 0.4-0.6 × 1.0-2.0μ |
| 2 | Cell pleomorphism | pleomorphic, showing snapping division |
| 3 | Motility | non motile |
| 4 | Sporulation | no sporulation |
| 5 | Gram stain | positive |
| 6 | Acid fast stain | non acid fast |

(b) Cultural Characterization

| | | Cultural characterization pH of culture media | |
|---|---|---|---|
| | Media | pH 7.0 | pH 10.0* |
| 1 | Nutrient agar plate | very poor growth | good growth, circular, flat to convex entire, cream, colored, opaque, smooth, glistening |

MORPHOLOGICAL, CULTURAL AND BIOCHEMICAL CHARACTERISTICS OF ARTHROBACTER FERM-P NO. 5863
-continued

| | | | |
|---|---|---|---|
| 2 | Nutrient agar slant | very poor growth | good growth, filiform |
| 3 | Nutrient broth | very poor growth | moderately tubid, no surface growth, sediment |
| 4 | Gelatin stab | very poor growth | surface growth, liquefaction, crateriform |
| 5 | Litmus milk | no change | no change |

(c) Biochemical characteristics*

| | | |
|---|---|---|
| 1 | Reduction of nitrate to nitrite | — |
| 2 | Nitrate respiration | — |
| 3 | Methyl red test | cannot observe the change of color because of alkaline medium |
| 4 | Voges-Proskauer test | — |
| 5 | Production of indole | — |
| 6 | Production of H$_2$S | — |
| 7 | Hydrolysis of starch | — |
| 8 | Utilization of citrate | |
| | Koser's citrate agar | + |
| | Christensen's citrate agar | + |
| 9 | Utilization of inorganic nitrogen source | utilize nitrates and ammonium salts |
| 10 | Production of pigment | none |
| 11 | Urease test | — |
| 12 | Oxidase test | — |
| 13 | Catalase test | + |
| 14 | pH and temperature for growth | |
| | pH for growth | 7.5–12.0 Optimum pH about 10 |
| | Temperature for growth | up to 42° C. Optimum temperature about 37° C. |
| 15 | Oxygen relation | aerobic |
| 16 | O-F test (Hugh and Leifson's medium) | aerobic growth |
| 17 | Utilization of carbohydrates | |
| | (1) L-Arabinose | + |
| | (2) D-Xylose | + |
| | (3) D-Glucose | + |
| | (4) D-Mannose | + |
| | (5) D-Fructose | + |
| | (6) D-Glactose | + |
| | (7) Maltose | + |
| | (8) Sucrose | + |
| | (9) Lactose | + |
| | (10) Trehalose | + |
| | (11) D-Sorbitol | + |
| | (12) D-Mannitol | + |
| | (13) Inositol | + |
| | (14) Glycerol | + |
| | (15) Starch | + |
| 18 | Another characteristics | |
| | (1) Cell walls do not contain meso-DAP. | |
| | (2) Cellulose not attacked. | |

*Na$_2$CO$_3$ (1%) was added to the media.
Symbols: +, positive; —, negative

MORPHOLOGICAL, CULTURAL AND BIOCHEMICAL CHARACTERISTICS OF ARTHROBACTER FERM-BP NO. 88

(a) Morphological characteristics

| | | |
|---|---|---|
| 1 | Cell form and size | rods, 0.4–0.6 × 1.0–2.0μ |
| 2 | Cell pleomorphism | pleomorphic, showing snapping division |
| 3 | Motility | non motile |
| 4 | Sporulation | no sporulation |
| 5 | Gram stain | positive |
| 6 | Acid fast stain | non acid fast |

(b) Cultural Characterization
-continued

MORPHOLOGICAL, CULTURAL AND BIOCHEMICAL CHARACTERISTICS OF ARTHROBACTER FERM-BP NO. 88

| | | Cultural characterization pH of culture media | |
|---|---|---|---|
| | Media | pH 7.0 | pH 10.0* |
| 1 | Nutrient agar plate | very poor growth | good growth, circular, flat, entire, cream, colored, opaque, smooth, glistening |
| 2 | Nutrient agar slant | very poor growth | good growth, filiform |
| 3 | Nutrient broth | very poor growth | moderately tubid, no surface growth moderate sediment |
| 4 | Gelatin stab | very poor growth | no liquefaction |
| 5 | Litmus milk | coagulated, partly peptonized | no change |

(c) Biochemical characteristics*

| | | |
|---|---|---|
| 1 | Reduction of nitrate to nitrite | — |
| 2 | Nitrate respiration | — |
| 3 | Methyl red test | cannot observe the change of color because of alkaline medium |
| 4 | Voges-Proskauer test | — |
| 5 | Production of indole | — |
| 6 | Production of H$_2$S | — |
| 7 | Hydrolysis of starch | — |
| 8 | Utilization of citrate | |
| | Koser's citrate agar | — |
| | Christensen's citrate agar | + |
| 9 | Utilization of inorganic nitrogen source | utilize nitrates and ammonium salts |
| 10 | Production of pigment | none |
| 11 | Urease test | — |
| 12 | Oxidase test | — |
| 13 | Catalase test | + |
| 14 | pH and temperature for growth | |
| | pH for growth | 7.5–12.0 Optimum pH about 10 |
| | Temperature for growth | up to 47° C. Optimum temperature about 40° C. |
| 15 | Oxygen relation | aerobic |
| 16 | O-F test (Hugh and Leifson's medium) | aerobic, anaerobic growth |
| 17 | Utilization of carbohydrates | |
| | (1) L-Arabinose | + |
| | (2) D-Xylose | + |
| | (3) D-Glucose | + |
| | (4) D-Mannose | + |
| | (5) D-Fructose | + |
| | (6) D-Glactose | + |
| | (7) Maltose | + |
| | (8) Sucrose | + |
| | (9) Lactose | + |
| | (10) Trehalose | + |
| | (11) D-Sorbitol | + |
| | (12) D-Mannitol | + |
| | (13) Inositol | + |
| | (14) Glycerol | + |
| | (15) Starch | + |
| 18 | Another characteristics | |
| | (1) Cell walls do not contain meso-DAP. | |
| | (2) Cellulose not attacked. | |

*Na$_2$CO$_3$ (1%) was added to the media.
Symbols: +, positive; —, negative

MORPHOLOGICAL, CULTURAL AND BIOCHEMICAL CHARACTERISTICS OF CORYNEBACTERIUM FERM-BP NO. 89

(a) Morphological characteristics

| | | |
|---|---|---|
| 1 | Cell form and size | rods, 0.4–0.6 × 0.8–1.2μ |

MORPHOLOGICAL, CULTURAL AND BIOCHEMICAL CHARACTERISTICS OF CORYNEBACTERIUM FERM-BP NO. 89

| | | |
|---|---|---|
| 2 | Cell pleomorphism | pleomorphic, showing snapping division |
| 3 | Motility | non motile |
| 4 | Sporulation | no sporulation |
| 5 | Gram stain | positive |
| 6 | Acid fast stain | non acid fast |

(b) Cultural Characterization

| | | Cultural characterization pH of culture media | |
|---|---|---|---|
| | Media | pH 7.0 | pH 10.0* |
| 1 | Nutrient agar plate | moderate growth | good growth, circular, flat, entire, cream, colored, opaque, smooth, glistening |
| 2 | Nutrient agar slant | moderate growth | good growth, filiform |
| 3 | Nutrient broth | very poor growth | very poor growth |
| 4 | Gelatin stab | moderate growth | surface growth, liquefaction crateriform |
| 5 | Litmus milk | acid, coagulated, partly peptonized | no change |

(c) Biochemical characteristics*

| | | |
|---|---|---|
| 1 | Reduction of nitrate to nitrite | − |
| 2 | Nitrate respiration | − |
| 3 | Methyl red test | cannot observe the change of color because of alkaline medium |
| 4 | Voges-Proskauer test | − |
| 5 | Production of indole | − |
| 6 | Production of H$_2$S | − |
| 7 | Hydrolysis of starch | − |
| 8 | Utilization of citrate | |
| | Koser's citrate agar | − |
| | Christensen's citrate agar | + |
| 9 | Utilization of inorganic nitrogen source | utilize nitrates and ammonium salts |
| 10 | Production of pigment | none |
| 11 | Urease test | − |
| 12 | Oxidase test | − |
| 13 | Catalase test | + |
| 14 | pH and temperature for growth | |
| | pH for growth | 6.5–12.0 Optimum pH about 10 |
| | Temperature for growth | up to 47° C. Optimum temperature about 40° C. |
| 15 | Oxygen relation | aerobic |
| 16 | O-F test (Hugh and Leifson's medium) | growth both aerobic anaerobic |
| 17 | Utilization of carbohydrates | |
| | (1) L-Arabinose | + |
| | (2) D-Xylose | + |
| | (3) D-Glucose | + |
| | (4) D-Mannose | + |
| | (5) D-Fructose | + |
| | (6) D-Glactose | + |
| | (7) Maltose | + |
| | (8) Sucrose | + |
| | (9) Lactose | + |
| | (10) Trehalose | + |
| | (11) D-Sorbitol | + |
| | (12) D-Mannitol | + |
| | (13) Inositol | + |
| | (14) Glycerol | + |
| | (15) Starch | + |
| 18 | Another characteristics | |
| | (1) Cell walls contain meso-DAP. | |

MORPHOLOGICAL, CULTURAL AND BIOCHEMICAL CHARACTERISTICS OF CORYNEBACTERIUM FERM-BP NO. 89

(2) Cellulose not attacked.

*Na$_2$CO$_3$ (1%) was added to the media.
Symbols: +, positive; −, negative

MORPHOLOGICAL, CULTURAL AND BIOCHEMICAL CHARACTERISTICS OF CORYNEBACTERIUM FERM-BP NO. 90

(a) Morphological characteristics

| | | |
|---|---|---|
| 1 | Cell form and size | rods, 0.4–0.5 × 0.5–1.0μ |
| 2 | Cell pleomorphism | pleomorphic, showing snapping division |
| 3 | Motility | non motile |
| 4 | Sporulation | no sporulation |
| 5 | Gram stain | positive |
| 6 | Acid fast stain | non acid fast |

(b) Cultural Characterization

| | | Cultural characterization pH of culture media | |
|---|---|---|---|
| | Media | pH 7.0 | pH 10.0* |
| 1 | Nutrient agar plate | moderate growth | good growth, circular, flat, entire, cream, colored, opaque, smooth, glistening |
| 2 | Nutrient agar slant | moderate growth | good growth, filiform |
| 3 | Nutrient broth | moderate growth | moderately tubid, no surface growth, moderate sediment |
| 4 | Gelatin stab | moderate growth | surface growth, liquefaction crateriform |
| 5 | Litmus milk | no change | no change |

(c) Biochemical characteristics*

| | | |
|---|---|---|
| 1 | Reduction of nitrate to nitrite | − |
| 2 | Nitrate respiration | − |
| 3 | Methyl red test | can not observe the change of color because of alkaline medium |
| 4 | Voges-Proskauer test | − |
| 5 | Production of indole | − |
| 6 | Production of H$_2$S | − |
| 7 | Hydrolysis of starch | − |
| 8 | Utilization of citrate | |
| | Koser's citrate agar | − |
| | Christensen's citrate agar | + |
| 9 | Utilization of inorganic nitrogen source | utilize nitrates and ammoniuum salts |
| 10 | Production of pigment | none |
| 11 | Urease test | − |
| 12 | Oxidase test | − |
| 13 | Catalase test | + |
| 14 | pH and temperature for growth | |
| | pH for growth | 6.5–12.0 Optimum pH about 10 |
| | Temperature for growth | up to 47° C. Optimum temperature about 40° C. |
| 15 | Oxygen relation | aerobic |
| 16 | O-F test (Hugh and Leifson's medium) | aerobic, anaerobic growth |
| 17 | Utilization of carbohydrates | |
| | (1) L-Arabinose | + |
| | (2) D-Xylose | + |
| | (3) D-Glucose | + |
| | (4) D-Mannose | + |
| | (5) D-Fructose | + |
| | (6) D-Glactose | + |
| | (7) Maltose | + |
| | (8) Sucrose | + |
| | (9) Lactose | + |
| | (10) Trehalose | + |
| | (11) D-Sorbitol | + |

MORPHOLOGICAL, CULTURAL AND BIOCHEMICAL CHARACTERISTICS OF CORYNEBACTERIUM FERM-BP NO. 90 -continued

|  |  |  |
|---|---|---|
|  | (12) D-Mannitol | + |
|  | (13) Inositol | + |
|  | (14) Glycerol | + |
|  | (15) Starch | + |
| 18 | Another characteristics |  |
|  | (1) Cell walls contain meso-DAP. |  |
|  | (2) Cellulose not attacked. |  |

*$Na_2CO_3$ (1%) was added to the media.
Symbols: +, positive; −, negative

MORPHOLOGICAL, CULTURAL AND BIOCHEMICAL CHARACTERISTICS OF BREVIBACTERIUM FERM-BP NO. 91

(a) Morphological characteristics

| | | |
|---|---|---|
| 1 | Cell form and size | short rods, 0.6–0.7 × 0.9–1.0μ |
| 2 | Cell pleomorphism | non pleomorphic |
| 3 | Motility | non motile |
| 4 | Sporulation | no sporulation |
| 5 | Gram stain | positive |
| 6 | Acid fast stain | non acid fast |

(b) Cultural Characterization

Cultural characterization pH of culture media

| | Media | pH 7.0 | pH 10.0* |
|---|---|---|---|
| 1 | Nutrient agar plate | very poor growth | good growth, circular, convex, entire, pale lemon yellow, opaque, smooth, glistening |
| 2 | Nutrient agar slant | very poor growth | good growth, filiform |
| 3 | Nutrient broth | very poor growth | slightly tubid, no surface growth, no sediment |
| 4 | Gelatin stab | very poor growth | surface growth, no liquefaction |
| 5 | Litmus milk | no change | no change |

(c) Biochemical characteristics*

| | | |
|---|---|---|
| 1 | Reduction of nitrate to nitrite | + |
| 2 | Nitrate respiration | − |
| 3 | Methyl red test | cannot observe the change of color because of alkaline medium |
| 4 | Voges-Proskauer test | − |
| 5 | Production of indole | − |
| 6 | Production of $H_2S$ | − |
| 7 | Hydrolysis of starch | − |
| 8 | Utilization of citrate | |
|  | Koser's citrate agar | − |
|  | Christensen's citrate agar | + |
| 9 | Utilization of inorganic nitrogen source | utilize nitrates and ammonium salts |
| 10 | Production of pigment | pale lemon yellow, not diffuse to the medium |
| 11 | Urease test | − |
| 12 | Oxidase test | − |
| 13 | Catalase test | + |
| 14 | pH and temperature for growth | |
|  | pH for growth | 7.5–12.5 Optimum pH about 10 |
|  | Temperature for growth | up to 47° C. Optimum temperature about 40° C. |
| 15 | Oxygen relation | aerobic |
| 16 | O-F test (Hugh and Leifson's medium) | aerobic, anaerobic growth |
| 17 | Utilization of carbohydrates | |
|  | (1) L-Arabinose | + |
|  | (2) D-Xylose | + |
|  | (3) D-Glucose | + |

MORPHOLOGICAL, CULTURAL AND BIOCHEMICAL CHARACTERISTICS OF BREVIBACTERIUM FERM-BP NO. 91 -continued

| | | |
|---|---|---|
|  | (4) D-Mannose | + |
|  | (5) D-Fructose | + |
|  | (6) D-Glactose | + |
|  | (7) Maltose | + |
|  | (8) Sucrose | + |
|  | (9) Lactose | + |
|  | (10) Trehalose | + |
|  | (11) D-Sorbitol | + |
|  | (12) D-Mannitol | + |
|  | (13) Inositol | + |
|  | (14) Glycerol | + |
|  | (15) Starch | + |
| 18 | Another characteristics | |

*$Na_2CO_3$ (1%) was added to the media.
Symbols: +, positive; −, negative

MORPHOLOGICAL, CULTURAL AND BIOCHEMICAL CHARACTERISTICS OF BREVIBACTERIUM FERM-BP NO. 92

(a) Morphological characteristics

| | | |
|---|---|---|
| 1 | Cell form and size | short rods, 0.4–0.5 × 0.6–1.2μ |
| 2 | Cell pleomorphism | non pleomorphic |
| 3 | Motility | non motile |
| 4 | Sporulation | no sporulation |
| 5 | Gram stain | positive |
| 6 | Acid fast stain | non acid fast |

(b) Cultural Characterization

Cultural characterization pH of culture media

| | Media | pH 7.0 | pH 10.0* |
|---|---|---|---|
| 1 | Nutrient agar plate | very poor growth | good growth, circular, convex, entire, pale lemon yellow, opaque, smooth, glistening |
| 2 | Nutrient agar slant | very poor growth | good growth, filiform |
| 3 | Nutrient broth | very poor growth | slightly tubid, no surface growth, no sediment |
| 4 | Gelatin stab | very poor growth | surface growth, no liquefaction |
| 5 | Litmus milk | no change | no change |

(c) Biochemical characteristics*

| | | |
|---|---|---|
| 1 | Reduction of nitrate to nitrite | − |
| 2 | Nitrate respiration | − |
| 3 | Methyl red test | cannot observe the change of color because of alkaline medium |
| 4 | Voges-Proskauer test | − |
| 5 | Production of indole | − |
| 6 | Production of $H_2S$ | − |
| 7 | Hydrolysis of starch | − |
| 8 | Utilization of citrate | |
|  | Koser's citrate agar | − |
|  | Christensen's citrate agar | + |
| 9 | Utilization of inorganic nitrogen source | utilize nitrates and ammonium salts |
| 10 | Production of pigment | pale lemon yellow, not diffuse to the medium |
| 11 | Urease test | − |
| 12 | Oxidase test | − |
| 13 | Catalase test | + |
| 14 | pH and temperature for growth | |
|  | pH for growth | 7.5–12.5 Optimum pH about 10 |
|  | Temperature for growth | up to 47° C. Optimum temperature about 40° C. |
| 15 | Oxygen relation | aerobic |
| 16 | O-F test (Hugh and | aerobic, anaerobic growth |

-continued

MORPHOLOGICAL, CULTURAL AND BIOCHEMICAL
CHARACTERISTICS OF BREVIBACTERIUM
FERM-BP NO. 92

| | Leifson's medium) | |
|---|---|---|
| 17 | Utilization of carbohydrates | |
| | (1) L-Arabinose | + |
| | (2) D-Xylose | + |
| | (3) D-Glucose | + |
| | (4) D-Mannose | + |
| | (5) D-Fructose | + |
| | (6) D-Glactose | + |
| | (7) Maltose | + |
| | (8) Sucrose | + |
| | (9) Lactose | + |
| | (10) Trehalose | + |
| | (11) D-Sorbitol | + |
| | (12) D-Mannitol | + |
| | (13) Inositol | + |
| | (14) Glycerol | + |
| | (15) Starch | + |
| 18 | Another characteristics | |

*$Na_2CO_3$ (1%) was added to the media.
Symbols: +, positive; −, negative

Both strains FERM-P Nos. 5861 and 5862 are aerobic, sporeforming gram positive, motile, rod shaped bacteria, with peritrichous flagella. It is clear that these two strains should belong to the genus Bacillus. The characteristic point of these bacteria was that they grew well in alkaline media rather than neutral media such as nutrient broth, the optimal pH for growth was about 10. The microbiological properties of these strains were similar to those of *Bacillus subtilis*. Both isolates, however, were distinguished from the typical strain *B. subtilis* in growth pH; Bacillus FEMP-P Nos. 5861 and 5862 grew better in alkaline media rather than in neutral media; and in Voges-Proskauer test; both isolates were negative but the typical strain *B. subtilis* is positive. The strain FERM-P No. 5861 was distinguished from the strain FERM-P No. 5862 in respect of cell size, production of $H_2S$ and production of acid from carbohydrates. Therefore, it is clear that these two strains are not the same.

Strains FERM-P No. 5863 and FERM-BP No. 88 are aerobic, non sporeforming rods, given gram positive, non acid fast, pleomorphic and showing snapping division. Furthermore, these two bacteria do not attack cellulose and the cell walls do not contain meso-DAP. It is clear that these two strains should belong to the genus Arthrobacter. The strain FERM-P No. 5863 was distinguished from the strain FERM-BP No. 88 in respect of cultural characterization in gelatin stab and litmus milk. Therefore, it is clear that these two strains are not the same.

Strains FERM-BP Nos. 89 and 90 are aerobic, non sporeforming rods, gram positive, non acid fast, pleomorphic and showing snapping division. Furthermore these two bacteria do not attack cellulose and the cell walls contain meso-DAP. It is clear that these two strains should belong to the genus Corynebacterium. The strain FERM-BP No. 89 was distinguished from the strain FERM-BP No. 90 in respect of cultural characterization in nutrient broth and litmus milk. Therefore, it is clear that these two strains are not the same.

Strains FERM-BP Nos. 91 and 92 are aerobic, non sporeforming short rods, gram positive, non acid fast, non pleomorphic, no branching or fragmentation. It is clear that these two strains should belong to the genus Brevibacterium. The strain FERM-BP No. 91 was distinguished from the strain FERM-BP No. 92 in respect of cell size and reduction of nitrate to nitrite. Therefore, it is clear that these two strains are not the same.

Taxonomic characteristics of strains FERM-P Nos. 5861, 5862 and 5863 and FERM-BP Nos. 88, 89, 90, 91 and 92 were investigated according to the method described in "Bergey's Manual of Determinative Bacteriology". These isolates were partly different from the typical strains in some properties. The characteristic point of these isolates was that they grow well in alkaline media rather than neutral media such as nutrient both, the optimal pH for growth is about 10.

The important cultivation condition of these bacteria is the pH of the culture medium. That is to say, when these bacteria are cultivated, the growth of *Bacillus* sp. FERM-P No. 5861 and FERM-P No. 5862, *Arthrobacter* sp. FERM-P No. 5863 and FERM-BP No. 88, Corynebacterium FERM-BP Nos. 89 and 90 and Brevibacterium FERM-BP Nos. 91 and 92 are largely affected by the pH of the culture medium. The desirable pH of the culture medium is within the range from 8.0 through 12.5. This is very convenient in the case where the above-mentioned microorganisms grow well in the alkaline extracted liquor or spent liquor obtained from alkaline pulping. According to the present invention, although the alkaline extracted liquor or spent liquor is used as a main carbon source, it should be noted that other carbon source substances which can be utilized by the microorganisms can also be used together with the extracted liquor or spent liquor.

In actual cultivation according to the present invention, inorganic nitrogen compounds such as ammonium salts and nitrates and nitrogen-containing organic substances such as urea and casein can be used as a nitrogen source. Furthermore, inorganic salts such as calcium salts, magnesium salts, potassium salts, phosphates, manganese salts, zinc salts, iron salts, and copper salts and, optionally, substances necessary to grow microorganisms or growth promoting agents such as vitamines, amino acids, corn steep liquor and yeast extract can be desirably added to the culture medium.

The cultivation of the present invention can be carried out by, for example, inoculating bacteria capable of growing in the alkaline extracted liquor or spent liquor obtained from alkaline pulping into the culture medium mentioned above, then conducting aerobic cultivation at a temperature of, for example, about 40° C. for 48 hours. Thus, the organic acids contained in the culture medium can be utilized. Thereafter, the cultivated product is subjected to a centrifugal operation at 5000 through 8000 rpm for 5 through 15 min, whereby the cultivated microbial bodies or cells are readily separated. The cells separated are collected and dried in a conventional manner to form the dried cells.

In order to further facilitate the cultivation operation and the separation and recovery operation of the cultivated bacteria according to the present invention, a pretreatment preventing the deposition or precipitation of the lignin component during the cultivation, such as the previous removal or oxidation of the lignin component in the alkaline extracted liquor or spent liquor can be advantageously carried out prior to the cultivation.

It has been determined that these cultivated cells obtained from the cultivation in the alkaline extracted liquor or spent liquor contain a large amount of crude proteins. Accordingly, the cultivated cells obtained from the cultivation of the present invention can be satisfactorily used as, for example, the protein-amino acid supply source, an animal feed, or a fish feed.

The present invention will be further illustrated by, but is by no means limited to, the following examples, in which all percentages are expressed on a weight basis unless otherwise specified.

EXAMPLE 1

Spent liquor derived from a soda pulping process and containing approximately 2.0% of organic acids, including isosaccharinic acid and metasaccharinic acid was adjusted in a pH of 10.0 by carbon dioxide. The precipitates formed by the addition of carbon dioxide were filtered through filter paper to obtain spent liquor having no substantial amount of suspended solids.

To the resultant spent liquor were added 0.2% of yeast extract, 0.15% of $K_2HPO_4$, 0.05% of $MgSO_4 \cdot 7H_2O$, and 0.5% of $KNO_3$. The pH thereof was then again adjusted to 10.0 by sodium carbonate.

Fifty ml portions of the culture medium prepared above were placed in 300 ml flasks and sterilized at a temperature of 120° C. for 15 minutes. *Bacillus* sp. FERM-P Nos. 5861 and 5862 and *Arthrobacter* sp. FERM-P No. 5863 were independently inoculated into the culture mediums.

Bacterial strains were subjected to shake culture at a temperature of 40° C. for 48 hours. The cells were centrifuged at 5000 rpm for 15 minutes and dried at a temperature of 100° C. for 24 hours. The amounts of the dried cells were as follows.

| Incubated bacterium | Amount of recovered cells (mg/ml of culture medium) |
| --- | --- |
| FERM-P No. 5861 | 7.5 |
| FERM-P No. 5862 | 6.5 |
| FERM-P No. 5863 | 8.0 |

The pH of each culture medium after the cultivation of the bacterium was 9.5 through 10.0. The amounts of the organic acids contained in the culture media after separating the cells of FERM-P Nos. 5861, 5862 and 5863 were 0.5%, 0.6%, and 0.2%, respectively.

As is clear from the above results, the organic acids contained in the spent liquor derived from the soda pulping process were utilized by the above-mentioned microorganisms under alkaline conditions, thereby being converted into the cells.

The crude protein contents in the dried cells of FERM-P Nos. 5861, 5862, and 5863 were 55%, 60%, and 55%, respectively.

EXAMPLE 2

Spent liquor derived from a kraft pulping process and containing approximately 3.0% of organic acids including isosaccharinic acid and metasaccharinic acid was adjusted in a pH of 9.5 by carbon dioxide. The precipitates formed by the addition of carbon dioxide were filtered through filter paper to obtain spent liquor having no substantial amount of suspended solids.

To the resultant spent liquor were added 0.2% of yeast extract, 0.15% of $K_2HPO_4$, 0.05%, or $MgSO_4 \cdot 7H_2O$, and 0.2% of urea. The pH thereof was then again adjusted to 9.5 by sodium carbonate.

Fifty ml portions of the culture medium prepared above were placed in 300 ml flasks and sterilized at a temperature of 120° C. for 15 minutes. *Bacillus* sp. FERM-P Nos. 5861 and 5862 and *Arthrobacter* sp. FERM-P No. 5863 were independently inoculated into the culture media.

After the inoculation, bacterial strains were subjected to shake culture at a temperature of 40° C. for 48 hours. The cells were centrifuged at 5000 rpm for 15 minutes and dried at a temperature of 100° C. for 24 hours. The amounts of and the crude protein contents in the dried cells were as follows.

| Incubated bacterium | Amount of recovered cells (mg/ml of culture medium) | Crude protein content (%) |
| --- | --- | --- |
| FERM-P No. 5861 | 7.5 | 54 |
| FERM-P No. 5862 | 8.0 | 59 |
| FERM-P No. 5863 | 9.5 | 53 |

The pH of each culture medium after the cultivation of the bacteria was 9.5 through 10.0.

As is clear from the above results, the organic acids contained in the spent liquor were effectively utilized by the above-mentioned microorganisms.

EXAMPLE 3

Example 1 was repeated, except that bacteria Arthrobacter FERM-BP No. 88, Corynebacterium FERM-BP Nos. 89 and 90 and Brevibacterium FERM-BP NOs. 91 and 92 were used and the content of the organic acids was approximately 5%. The results were as follows.

| Incubated bacterium | Amounts of recovered cells (mg/ml of culture medium) | Amounts of organic acids in culture medium | Crude protein content |
| --- | --- | --- | --- |
| FERM-BP No. 88 | 15.5 | 0.4% | 60% |
| FERM-BP No. 89 | 9.5 | 1.6 | 62 |
| FERM-BP No. 90 | 10.0 | 1.5 | 58 |
| FERM-BP No. 91 | 12.0 | 0.6 | 58 |
| FERM-BP No. 92 | 11.5 | 0.8 | 56 |

EXAMPLE 4

Example 2 was repeated except that bacteria Arthrobacter FERM-BP No. 88, Corynebacterium FERM-BP Nos. 89 and 90 and Brevibacterium FERM-BP Nos. 91 and 92 were used the content of the organic acids was approximately 6% and the pH was adjusted to 10.5. The results were as follows.

| Incubated bacterium | Amounts of recovered cells (mg/ml of culture medium) | Crude protein content (%) |
| --- | --- | --- |
| FERM-BP-No. 88 | 16.5 | 58 |
| FERM-BP-No. 89 | 10.0 | 60 |
| FERM-BP-No. 90 | 11.0 | 58 |
| FERM-BP-No. 91 | 14.5 | 60 |
| FERM-BP-No. 92 | 13.5 | 56 |
| FERM-BP-Nos. 89 and 91 | 20.0 | 60 |

The *Bacillus* sp. FERM-P Nos. 5861 and 5862 and the 11 Arthrobacter sp. FERM-P No. 5863 were redeposited on Feb. 5, 1982, as an effective deposition date of May 1, 1981, in the Fermentation Research Institute (FRI) in Japan under the Budapest Treaty as FERM-BP Nos. 97, 98 and 99, respectively.

We claim:

1. A method for cultivating a microorganism comprising the steps of:
   inoculating at least one microorganism which grows well under alkaline conditions and is selected from the group consisting of *Bacillus* SP. FERM-P No. 5861 and SP. FERM-P No. 5862, *Arthrobacter* SP. FERM-P No. 5863 and SP. FERM-BP No. 88, *Corynebacterium* SP. FERM-BP Nos. 89 and 90, and *Brevibacterium* FERM-BP Nos. 91 and 92, into a culture medium containing, as a carbon source, extracted liquor or spent liquor derived from alkaline pulping; and cultivating the inoculated microorganism in the culture medium at a pH of 8.0 to 12.5 under an aerobic condition; whereby organic acids contained in the extracted liquor or spent liquor are utilized.

2. A method as claimed in claim 1, wherein the cultivated cells obtained from the cultivation are recovered.

* * * * *

UNITED STATES PATENT AND TRADEMARK OFFICE
CERTIFICATE OF CORRECTION

PATENT NO. : 4,514,501
DATED : April 30, 1985
INVENTOR(S) : YUKIO KITA ET AL

It is certified that error appears in the above-identified patent and that said Letters Patent is hereby corrected as shown below:

On the cover page, Item [75], change "Kouki Horiko" to --- Kouki Horikoshi ---.

Signed and Sealed this

Eighth Day of October 1985

[SEAL]

Attest:

DONALD J. QUIGG

Attesting Officer

Commissioner of Patents and Trademarks—Designate